US00PP14387P29

(12) United States Plant Patent
Anderson

(10) Patent No.: US PP14,387 P2
(45) Date of Patent: Dec. 16, 2003

(54) DAHLIA PLANT NAMED 'BALNOVOST'

(50) Latin Name: *Dahlia pinnata*
Varietal Denomination: Balnovost

(75) Inventor: Neil Anderson, St. Paul, MN (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,506

(22) Filed: Mar. 27, 2002

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—Wood, Phillips, Katz, Clark & Mortimer

(57) ABSTRACT

A new and distinct Dahlia plant named 'Balnovost', characterized by its semi-double lavender and white bicolor ray florets, upright mounded form and moderately vigorous growth habit, is provided.

1 Drawing Sheet

Latin name of genus and species of plant claimed: *Dahlia pinnata.*
Variety denomination: 'Balnovost'.

BACKGROUND OF THE INVENTION

The present invention comprises a new and distinct Dahlia plant, botanically known as *Dahlia pinnata* and hereinafter referred to by the cultivar name 'Balnovost'.

The new cultivar is the product of a planned breeding program. The female (seed) parent of the new cultivar was 'Figaro White' (unpatented) which exhibits white flowers. The male (pollen) parent of the new Cultivar was a mix of pollen from the *Dahlia pinnata* series 'Figaro Improved', which exhibits flowers of red, rose, mauve, salmon, yellow or white. The new cultivar was discovered and selected as a single flowering plant from within the progeny of the above stated cross during 1998–1999 in Elburn, Ill. and was initially designated PAS11428-4.

Asexual reproduction of the new cultivar by terminal tip cuttings taken during 2001 at West Chicago, Ill., has demonstrated that the characteristics of the new cultivar as herein described are firmly fixed and reproduced true to type through successive generations of such asexual propagation.

SUMMARY OF THE INVENTION

It was found that the cultivar of the present invention:

(a) forms semi-double inflorescences with lavender and white bicolor ray florets;

(b) exhibits an upright mounded form; and (c) exhibits a moderately vigorous growth habit.

'Balnovost' has not been observed under all possible environmental conditions to date. Accordingly, it is possible that the phenotype may vary somewhat with variations in the environment, such as temperature, light intensity, and day length without, however, any variance in genotype.

The new cultivar of the present invention can be compared to 'Betty' (U.S. Plant Pat. No. 7,762). However, in side-by-side comparisons, 'Balnovost' exhibits shorter branches and lighter colored, larger flowers with fewer but larger ray florets.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for nine weeks in a greenhouse at West Chicago, Ill.

DETAILED BOTANICAL DESCRIPTION

The chart used in the identification of colors described herein is The R.H.S. Colour Chart of The Royal Horticultural Society, London, England. The color values were determined on Nov. 21, 2001 in West Chicago, Ill. The readings were taken between 10:00 and 11:45 p.m. under natural light conditions. The plants were produced from cuttings taken from stock plants and were grown in a double polycarbonate covered greenhouse under conditions comparable to those used in commercial practice. The plants were grown while utilizing a soilless growth medium and maintaining temperatures of approximately 65 ° to 70° F. (18° to 21° C.) during the day and approximately 60° to 65° F. (15° to 18° C.) during the night. Light levels of 4,000 to 6,000 footcandles were maintained. Plants were pinched at three weeks after planting. The following measurements and descriptions describe plants grown in West Chicago, Ill. for nine (9) weeks after planting of rooted cuttings.

Classification:
*Botanical.*—*Dahlia pinnata* cultivar 'Balnovost'.
*Commercial.*—Dahlia.

Parentage:
*Female parent.*—Figaro 'White'.
*Male parent.*—Mix of pollen from the series 'Figaro Improved'.

Propagation:
*Type cutting.*—Terminal tip.
*Time to initiate roots.*—Approximately 10 to 14 days.
*Time to develop roots.*—Approximately 21 to 28 days.
*Root description/habit.*—Fibrous and well branched.
*Tubers.*—Will form under short day conditions of at least 13 to 14 hours of darkness.

Plant description:

*General appearance and form.*—Upright and mounded, moderately vigorous.

*Height above pot.*—Foliage only: Approximately 11.4 cm. Whole plant: Approximately 19.3 cm.

*Width.*—Approximately 17.5 cm.

*Branching habit.*—Freely branching. Pinching 14 to 21 days after transplanting helps to improve basal branching.

*Branch description.*—Length: Approximately 6.6 cm. Diameter: Approximately 4 mm. Color: 146B. Texture: Smooth. Internode length: Approximately 1.6 cm.

Foliage description:

*Form.*—Mature foliage consists of both simple and compound leaves.

*Shape.*—Ovate.

*Margin.*—Serrate.

*Apex.*—Acute.

*Base.*—Attenuate.

*Arrangement.*—Opposite.

*Venation pattern.*—Pinnate, reticulate.

*Surface.*—Upper surface is rough, dull and slightly rugose. Lower surface is dull.

*Color of mature foliage.*—Upper surface: 137A with veins of 146B.

*Color of mature foliage.*—Lower surface: Closest to 191B with veins of 138A.

*Size.*—Single mature leaf is approximately 7 cm in length and 5.2 cm in width. Mature compound (trifoliate) leaf is approximately 7.5 cm in length and 7.8 cm in width. Terminal leaflet is approximately 6 cm in length and 4.2 cm in width. Lateral leaflets are apporoximately 3.8 cm in length and 2.5 cm in width and sessile.

*Petiole of simple mature leaf.*—Approximately 3.5 cm in length 4 mm in diameter and color of 145A. Petiole of compound (trifoliate) leaf — Approximately 4 cm in length, 3 mm in diameter and color of 146B. Petiole of terminal leaflet of trifoliate leaf — Approximately 1 cm in length, 2 mm in diameter and color of 145A.

Inflorescence description:

*Outdoor flowering habit.*—'Balnovost' is freely flowering under outdoor growing conditions with substantially continuous blooming from spring through fall.

*Lastingness of individual bloom.*—Approximately ten (10) days.

*Fragrance.*—None.

*Response time.*—Approximately six (6) weeks from planting of rooted cutting.

*Number of blooms per plant.*—Approximately four (4).

*Appearance.*—Semi-double, arising from leaf axils on strong peduncles. Disc and ray florets arranged acropetally on a capitulum.

*Inflorescence bud.*—Shape: Round. Length: Approximately 1.6 cm. Diameter: Approximately 1.6 cm. Color: Darker than 71A.

*Inflorescence size.*—Diameter: Approximately 7.1 cm. Depth: Approximately 1.4 cm. Disc diameter: Approximately 2.3 cm.

*Ray florets.*—Quantity: Approximately 32 per flower. Shape: Elongated, cupped. Length: Approximately 3.3 cm. Width: Approximately 2.2 cm. Apex: Pointed to slightly rounded. Base: Attenuate. Margin: Entire. Texture: Smooth. Color: At opening — 71B at margin (outer ¼ of surface), 73D in center (middle ¼ of surface) 155D near base (⅜ of surface) 3C at base (lowest ⅛). Fully opened, upper surface: 74A at margin, 73C/D in center and 2A at base. Lower surface of ray florets is 70A at margin, 73D in center and 150C at base.

*Disc florets.*—Number per Inflorecence: Approximately 63. Shape: Elongated, cylindrical. Length: Approximately 8 mm. Diameter: Approximately 2 mm. Color: 7A, transparent.

*Receptacle.*—Diameter: Approximately 2 cm. Height: Approximately 3 mm.

*Peduncle.*—Strong, erect. Length: Approximately 11 cm. Texture: Smooth. Color: 146C.

*Involucral bracts.*—Quantity: 12. Shape: Diamond-shaped. Tip: Broadly acute. Margin: Entire. Length: Approximately 1.1 cm. Width: Approximately 7 mm. Texture: Smooth. Color of both upper and lower surfaces:144A with venation of 143A.

*Reproductive organs.*—Androecium — On disc florets. Anthers approximately 4 mm in length and 13A filaments are 1 cm 13A. Gynoecium — On disc and ray florets. Pistil length: Approximately 8 mm. Stigma length is 2 mm. Style length is 3 mm. Pollen: Abundant, 24A. Ovary length is 3 mm and color closest to 150B.

*Seed production.*—Seed production has not been observed.

*Disease resistance.*—Disease resistance has not been observed.

*Weather tolerance.*—The weather tolerance of the new Dahlia has been shown to be typical for Dahlias.

I claim:

1. A new and distinct Dahlia plant named 'Balnovost' substantially as herein shown and described, which:

(a) exhibits an upright mounded form;

(b) forms semi-double inflorescences with lavender and white bicolor ray florets; and (c) exhibits a moderately vigorous growth habit.

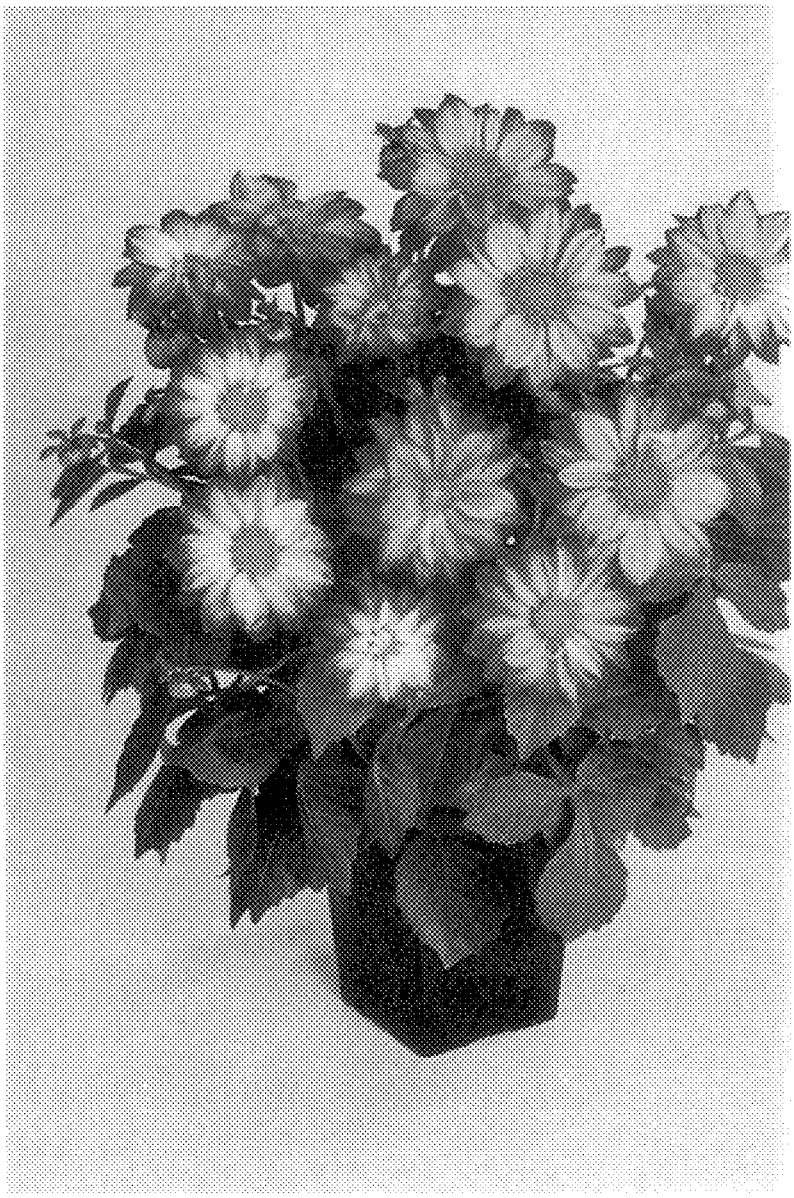

* * * * *